United States Patent [19]

Laumen

[11] Patent Number: 4,912,042
[45] Date of Patent: Mar. 27, 1990

[54] PREPARATION OF D-MALIC ACID OR DERIVATIVE

[75] Inventor: Kurt E. Laumen, Wuppertal, Fed. Rep. of Germany

[73] Assignee: Eastman Kodak Company, Rochester, N.Y.

[21] Appl. No.: 395,003

[22] Filed: Aug. 17, 1989

[51] Int. Cl.$^4$ .................... C12P 7/02; C12R 1/01; C07P 41/00
[52] U.S. Cl. .................... 435/145; 435/135; 435/136; 435/280; 435/822; 435/874
[58] Field of Search .............. 435/280, 145, 822, 874, 435/135, 136

[56] References Cited

U.S. PATENT DOCUMENTS

| | | | |
|---|---|---|---|
| 2,314,831 | 3/1943 | Kamuet | 435/145 |
| 2,972,566 | 2/1961 | Kitahara | 435/145 |
| 3,063,910 | 11/1962 | Abe et al. | 435/145 |
| 3,600,279 | 8/1971 | Takahashi et al. | |
| 3,907,638 | 9/1975 | Uzuki et al. | |
| 3,957,579 | 5/1976 | Sato et al. | 435/145 |
| 3,971,700 | 7/1976 | Boesten | 435/280 |
| 3,980,520 | 9/1976 | Degen et al. | |
| 4,092,220 | 5/1978 | Tsurumi et al. | 435/280 |
| 4,094,741 | 6/1978 | Vamada et al. | 435/280 |
| 4,148,688 | 4/1979 | Yamada et al. | |
| 4,629,701 | 12/1986 | Sakimae et al. | |
| 4,636,470 | 1/1987 | Empie | |
| 4,745,061 | 5/1988 | Aretz et al. | |
| 4,751,182 | 6/1988 | Sih | |
| 4,758,518 | 7/1988 | Taylor | |

FOREIGN PATENT DOCUMENTS

| | | | |
|---|---|---|---|
| 0207636 | 1/1987 | European Pat. Off. | |
| 0014786 | 7/1969 | Japan | 435/145 |
| 0008634 | 3/1970 | Japan | 435/280 |
| 0008671 | 1/1972 | Japan | 435/280 |
| 0008591 | 3/1972 | Japan | 435/280 |
| 50-024490 | 3/1975 | Japan | |
| 50-040787 | 4/1975 | Japan | |
| 0079783 | 7/1976 | Japan | 435/145 |
| 0155096 | 9/1983 | Japan | 435/280 |
| 2019098 | 1/1987 | Japan | 435/280 |
| 2118899 | 5/1987 | Japan | 435/280 |
| 3091097 | 4/1988 | Japan | 435/280 |
| 63-141597 | 6/1988 | Japan | |
| 0463670 | 3/1975 | U.S.S.R. | 435/280 |
| 1198530 | 7/1970 | United Kingdom | 435/280 |
| 2175304 | 11/1986 | United Kingdom | 435/145 |

OTHER PUBLICATIONS

Chem. Abs. vol. 70 (1969) 65443m Hopper et al., Biochem. J. 1968 110(4), 798–800.
Chem. Abs. vol. 74 (1971) 39578x Hopper et al.

*Primary Examiner*—Herbert J. Lilling
*Attorney, Agent, or Firm*—Robert A. Linn

[57] ABSTRACT

D-malic acid is produced from D,L-malic acid by subjecting the racemate to the action of a microorganism or product thereof which assimilates L-malic acid but not D-malic acid, until the L-malic acid in the racemate is substantially consumed. D-malic acid recovered from the reaction mixture has a high degree of optical purity. Preferred microorganisms are bacteria such as *Pseudomonas putida* and *Acinetobacter calcoaceticus*.

9 Claims, No Drawings

PREPARATION OF D-MALIC ACID OR DERIVATIVE

FIELD OF THE INVENTION

This invention relates to D-malic acid, and particularly to its preparation from D,L-malic acid. In a preferred embodiment, the process of this invention comprises contacting D,L-malic acid with a living microorganism (or a product thereof) which assimilates L-malic acid but not the D-isomer. Thus, the invention relates to the resolution of a racemic mixture of malic acids via use of a microorganism which can assimilate only one of the two isomers present in the racemate. The D-malic acid can be used as a chemical intermediate, or to resolve a racemic mixture of bases. D-malic acid derivatives can be prepared by the process of this invention.

BACKGROUND OF THE INVENTION

It is known in the art that racemates can be reacted with optically active compounds to form diastereomers that can be separated. Thus, it is known that racemic mixtures of acids can be separated by a process which comprises reacting the racemate with an optically active base such as quinine, and then separating the diastereomers thereby produced by a technique such as fractional crystallization. This type of separation technique is time-consuming and expensive.

RELATED ART

Applicant is unaware of a prior art process using microorganisms for the preparation of D-malic acid, or a derivative thereof.

Degen et al, U.S. Pat. No. 3,980,520 relates to the formation of L-malic acid from fumaric acid by a fermentation technique that uses the enzyme fumarase. The disclosed process entails use of a microorganism not employed before as a fumarase source. As stated in the patent, it is known in the art that the reaction can proceed in both ways, so that it is possible to use fumarase to prepare malic acid from fumaric acid, or fumaric acid from malic acid. L-malic acid is the optical isomer which occurs in nature.

U.S. Pat. No. 3,600,279 pertains to a method for producing D-pantoic acid from D,L-pantoic acid. A culture medium comprising the racemate is inoculated with an enzyme which assimilates L-pantoic acid but which does not assimilate D-pantoic acid. Then, the culture is incubated until the L-pantoic acid is substantially consumed. Thereafter, the unassimilated D-pantoic acid is recovered from the reaction mixture.

U.S. Pat. No. 3,907,638 pertains to a solvent system comprising an organic phase and an aqueous phase, useful in the selective deacylation of N-acyl-D,L-amino acids. A racemate is contacted with an acylase which deacylates only one enantiomer but not the other, and the amino acid produced is recovered from the aqueous phase. The carboxylic acid produced from the acyl group, and the non-hydrolyzed acyl amino acid, are recovered from the organic phase.

U.S. Pat. No. 4,148,688 discloses a method for preparing L-methionine. The process comprises subjecting DL-N-carbamoylmethionine to a microorganism capable of hydrolyzing the L-N-carbamoylmethionine.

U.S. Pat. No. 4,629,701 discloses a process for producing an optically active carboxylic acid which comprises contacting an ester of the defined racemic acid with an enzyme or microorganism that is capable of asymmetrically hydrolyzing an ester bond.

U.S. Pat. No. 4,636,470 relates to use of a two-phase solvent system in the resolution of racemates of amino acids. In the method, one of the optical isomers of the racemate is enzymatically hydrolyzed to the corresponding amino acid, and recovered.

U.S. Pat. No. 4,751,182 relates to a process for resolving DL-carnitine. The process comprises cont acting a racemate which preferentially metabolizes the unnatural D-form of the compound, thereby permitting the natural isomer, L-carnitine to accumulate in the reaction medium.

U.S. Pat. No. 4,745,061 pertains to a transaminase useful for resolving DL-amino acids by attacking the D-isomer to form the corresponding keto acid.

U.S. Pat. No. 4,758,518 pertains to a hydrolase used to increase the concentration of L-enantiomer in a mixture of D and L isomers of a 2-haloalkanoic acid.

European Patent Application 207,636 teaches a process for producing an optically enriched 2,3-dichloro-1-propanol from a racemic mixture which comprises cultivating a strain of Pseudomonas which assimilates the undesired enantiomer in the racemate.

Japan 63 141,597 teaches the preparation of optically pure L-lactic acid by treating a racemic mixture with a microorganism having an ability to use D-lactic acid.

Japan 50 040,787 discloses the preparation of D-phenylglycine from a racemic mixture using an organism which oxidizes or assimilates the L-antipode.

Japan 50 024,490 discloses the preparation of D-tartaric acid from DL-tartaric acid by culturing a microorganism with the racemate until the L-tartrate is completely assimilated.

None of the references noted above discloses a method for resolving a racemic mixture of D- and L-malic acids, or a racemic mixture of D- and L-malic acid esters, amides or similar derivatives of malic acid.

Applicant's invention comprises the discovery of microorganisms that will assimilate L-malic acid and not assimilate D-malic acid. Furthermore, the invention comprises application of this discovery to the separation of one malic acid enantiomer from the other. In Applicant's studies of process, it was discovered that the presence of D-malic acid might inhibit the assimilation of L-malic acid, and it was also discovered that the inhibitory effect can be efficaciously overcome by maintaining the D-malic acid concentration at an acceptably low level. Applicant's work also demonstrated that an organism utilized in the process can be inhibited by acidity loss caused by assimilation of the L-malic acid. Thus, in a preferred embodiment for preparing D-malic acid in comparatively high purity. Applicant provides the step of replenishing the acidity loss, so that the pH remains below an inhibitory value.

Applicant's process provides several advantages. First, it provides a means for preparing D-malic acid in a high state of optical purity. It also provides means for resolving a racemic mixture of D- and L-malic acids by substantial consumption of the L enantiomer. The method is economical and is not overly time-consuming. Furthermore, it does not entail the tedious use of expensive compounds such as quinine. It can be used as a basis for the preparation of D-malic acid in commercial quantities.

SUMMARY OF THE INVENTION

This invention relates to the preparation of D-malic acid. In the process of this invention, D-malic acid is separated from a mixture of that substance and its enantiomer L-malic acid. In a preferred embodiment, a racemic mixture of the optical antipodes is resolved.

The process entails use of a microorganism which is capable of assimilating L-malic acid but not D-malic acid. Of the microorganisms having these properties, bacteria are preferred. Such bacteria are exemplified by *Pseudomonas putida* and *Acinetobacter calcoaceticus*. These bacteria are capable of assimilating L-malic acid as an energy and sole carbon source, while not requiring the presence of supplements such as vitamins.

This invention comprises the discovery that microorganisms, such as the bacteria named above, can be inhibited by the presence of D-malic acid. In such instances, it is preferred to conduct the process of this invention at a D-malic acid concentration below that at which the process is severely inhibited. Thus, in preferred embodiments, it is preferred that the process be conducted at a D-malic acid concentration below about 5.0, more preferably below about 2.5 weight percent.

It has also been discovered that the decrease in acidity caused by assimilation of L-malic acid can adversely effect the reaction. More specifically a decrease in acidity can inhibit the assimilation of L-malic acid, and thereby afford a less complete separation of D- and L-malic acid. Therefore, the process is preferably conducted by replenishing the acid lost by assimilation of the L-malic acid. The added acid keeps the pH below about 9.0: above that pH process inhibition may be significant.

The process of this invention is not dependent on any single metabolic mechanism. In other words, it is not necessary that the microorganism assimilate the L-malic acid in any particular manner. Thus, for example, a microorganism suitable for use in this invention may utilize the L-malic acid in the citric acid cycle; however, it is not necessary that it do so. All that is necessary is that the organism utilize L-malic acid, and not transform the D-malic acid in any manner to an undesirable extent.

The invention is particularly directed to the use of microorganisms that will utilize L-malic acid as an energy and sole carbon source. Such organisms make the process less expensive and easier to carry out. As indicated above, preferred microorganisms are bacteria. Fungi (including yeasts and molds) can also be employed.

D-malic acid derivatives can be prepared by the process of this invention.

DESCRIPTION OF PREFERRED EMBODIMENTS

This invention provides a process for the preparation of D-malic acid or a D-malic acid derivative from a mixture of D-malic and L-malic acid or a mixture of a D-malic acid derivatives and the equivalent derivative of L-malic acid, by treating said mixture with a resolution agent, said agent comprising a living microorganism (or product thereof) capable of assimilating L-malic acid or derivative, but incapable of assimilating D-malic acid or derivative; (ii) incubating said agent and mixture until substantially all of the L-malic acid or derivative is assimilated; and (iii) thereafter recovering D-malic acid or derivative from the reaction broth thereby produced.

In a preferred embodiment, this invention comprises a process for separating D-malic acid from a mixture of that substance and L-malic acid, said process comprising subjecting said mixture to the action of bacteria capable of assimilating L-malic acid and incapable of assimilating D-malic acid, until substantially all said L-malic acid is assimilated, said process being conducted in the presence of acid added to replenish acidity loss due to the assimilation of L-malic acid and to thereby maintain the pH below about 9.0. The added acid can be added intermittently or continuously over the period while the L-malic acid is being assimilated.

In a highly preferred embodiment, this invention provides a process for the preparation of D-malic acid in enantiomeric excess of at least about 90% from a racemic mixture of D-malic acid and L-malic acid, said process comprising subjecting said racemic mixture to the action of bacteria (a) capable of assimilating L-malic acid as a sole energy and carbon source in the absence of any added supplement, and (b) incapable of assimilating D-malic acid; until substantially all of the L-malic acid is consumed, said process being conducted such that (i) the concentration of D-malic acid in the reaction mixture comprising said bacteria does not exceed about 5.0, more preferably below about 2.5 weight percent, and (ii) acid is added during said process to replenish the acidity loss due to assimilation of L-malic acid and to maintain the pH of the reaction mixture between about 4.5 and about 9.0.

This invention can be conducted using any microorganism which is capable of assimilating L-malic acid or a derivative thereof such as an ester of amide, and incapable of assimilating D-malic acid or a derivative of D-malic acid. Such microorganisms are selected from wild isolates, strains deposited in public organizations, and strains obtained by mutation of such strains. As an examining method, a typical basal agar plate medium for screening contains 0.2% ammonium sulfate, 0.2% $K_2HPO_4$, 0.002% yeast extract and 10 mL salt solution C and 15 g Agar in 1 L of water, adjusted to pH 7.0 with HCl, then sterilized. As the main carbon source, 0.5 to 1.0 weight percent D-malic acid or L-malic acid is added to the basal medium (as a 20% sterile-filtered solution whose pH had been adjusted to 7.00) in order to prepare two kinds of test media, one containing D-malic acid, the other containing L-malic acid. Agar plates having each type of media are prepared.

A microorganism to be screened is inoculated on both types of agar plates and incubated for up to several days at their optical growth temperature. Such temperatures typically can be in the range of 28°–35° C. For some organisms, optimal growth temperatures may be outside this range. Microorganisms for use in this invention are selected from those which grow on a plate containing L-malic acid and which do not grow on a plate containing D-malic acid.

In some instances, microorganisms that cannot assimilate D-malic acid may grow on the plate in which that substance is supplied as the energy and carbon source. The minimal amount of growth is the result of utilization of the yeast extract or other nutrient incorporated in the growth medium.

If desired, a similar screening technique can be applied using as a carbon source or malic acid derivatives such as L-malic acid ethyl ester or L-malic acid amide, and D-malic acid ethyl ester or D-malic acid amide in place of L- and D-malic acid, respectively.

In the practice of this invention, organisms that will assimilate L-malic acid or derivative and not assimilate D-malic acid or derivative, and which can use the L-malic acid or derivative as a sole energy and carbon source, are preferred. Such organisms can be made to interact with the mixture of malic acids or derivatives by using the living organism in a culture medium thereof. Alternatively, the organism can be anchored or bound to a substrate. In addition, enzyme preparations may be used in the form of a cell-free extract, crude enzyme, or purified enzyme. The enzyme preparation can be made from the cells or the culture medium according to conventional methods. If desired, enzymes can be immobilized by attachment to a substrate and used in this invention.

The amount of microorganism used in the practice of this invention is the amount required to assimilate all or substantially all of the L-malic acid or derivative in the mixture of malic acids or derivatives being treated. Generally, the amount of microorganism used is in the weight ratio of from about 0.005 to about 5.0; that ratio being in terms of the dry weight of cells compared to the weight of the malic acid (or derivative) mixture. In those instances where immobilized organisms or enzyme preparations are used, the amount employed can be determined by using as a basis the weight of the cells from which the employed substance is derived.

When an immobilized enzyme or microorganism is used in the practice of this invention, a conventional carrier can be employed as the medium on which the organism or enzyme is bound. Examples of carriers that may be used in the invention include natural products such as alginic acid, carrageenan, collagen, cellulose, acetylcellulose, agar cellophane, and collodion and synthetic polymer substances such as polyacrylamide, polyurethane, and polybutadiene. The immobilization of the cells or enzyme on the carrier can be carried out in a conventional method under moderate conditions so that the activity of the biocatalyst is not impaired.

The process temperature employed is dependent on the microorganism or extract thereof. In some instances it can be in the range of from about 20° C. to about 50° C. Generally, the temperature is not permitted to exceed about 35° C. for an extended period of time. A preferred temperature range is from about 28° C. to about 35° C.

The process is carried out under aerobic conditions. As customary in the art, enhanced oxygen contact with the reaction zone can be effected by shaking, or by rocking the vessel in which the process is conducted, or by stirring the vessel contents. Air, or air admixed with oxygen, can be admitted to the fermentation vessel, either as a fine stream or a stream of bubbles introduced into the fermenting liquid.

The fermentation time is not a truly independent variable, but is dependent at least in part on other variables such as the process temperatures, the amount of microorganisms or other resolution agent employed, and the activity thereof. In general, the process time can be within the range of from about two to about 50 hours. Higher process temperatures and more active resolution agents favor shorter reaction periods.

The process can be conducted by initially adding all of the microorganism (or enzyme preparation) to all of the malic acid mixture (or the mixture of malic acid derivatives). Alternatively, the resolution agent and/or the malic acid (or derivative) mixture can be added continuously, or from time to time, over the course of the fermentation.

As mentioned above, the D-malic acid might inhibit the reaction of its concentration in the fermentation medium is too high. The mechanism by which any inhibition takes place is not known with certainty at this time.

Although not bound by any theory, it is believed that in some instances there may be some competitive inhibition due to competition between the malic acid isomers for active enzyme sites. To combat the inhibition, an operator may use any convenient expedient to maintain the concentration of the D-malic acid at a suitable level. For example, with certain bacteria better results are obtained if the level of D-malic acid is kept below about 5.0, more preferably below about 2.5 weight percent.

Preferably, the process is conducted at a pH of at least about neutral, i.e., 7.0. To achieve this level, a buffer is employed. If the process is carried out at a pH outsideof this range, it may be too slow to be practical.

There is a tendency for the pH to rise as L-malic acid is assimilated. If the capacity of the buffer is exceeded, the pH may exceed 9.0 and cause an inhibition of the reaction. Thus, it is desirable to replenish the acidity loss during the course of a process using L-malic acid. The replenishment can be made to take place automatically, by linking an acid source to a device which introduces acid into the reaction mixture in response to a continuous monitoring of the pH level. The added acid may be any convenient biologically acceptable acid, such as dilute hydrochloric or sulfuric acid, or malic acid.

EXAMPLE (I) A 500 ml shaking flask containing 100 ml of a L-malic acid (I) solution was inoculated with one loop of *Pseudomonas putida* ATCC 21244 (from an agar plate containing L-malic acid as the energy and carbon source). The inoculated solution was incubated at 30° C. while shaking at 200 rpm. The final optical density (O.D) at 660 nanometers was 1.475. The malic acid solution had the following composition:

L-Malic acid Solution (I)

```
2 g (NH4)2SO4
2 g K2HPO4
10 ml Salt solution C (II)
4 g L-malic acid
plus H2O and NaOH to make 1 liter of pH
7.0 solution. The solution was sterilized
by filtration (0.2 mµ filter)
```

Salt Solution C (II) (mentioned above) had the following composition:

```
25 g MgSO4.7H2O
2.8 g FeSO4.7H2O
1.7 g MnSO4.H2O
0.6 g NaCl
0.1 g CaCl2.2H2O
0.1 g NaMoO4.2H2O
0.06 g ZnSO4.7H2O
in one liter of ~0.1 N HCl
```

(II) A one liter fermenting flask containing Solution (III) was sterilized.
Solution (III)

```
70 mg Dow Antifoam
2 g (NH4)2SO4
2 g K2HPO4
HCl and H2O were added to make 750 ml of a
pH 7.0 solution sterilized by filtration
(0.2 μm filter)
```

After the temperature of the fermenter solution reached 30° C., Solution (IV) was added. Solution (IV) was prepared as follows:

Solution (IV)

```
10 g DL-malic acid
10 ml Salt Solution C (II)
NaOH and H2O were added to make 150 ml of
a pH 7.0 solution which was sterilized by
filtration using a 0.2 μm filter.
```

Thereafter, the bacteria suspension prepared in Step (I) was added to the fermenter. Air was introduced into the fermenter at the rate of 1 liter/minute. The temperature was maintained at 30° C. and the fermenter contents were stirred at 1000 rpm to maintain the dissolved oxygen content greater than 60–70% saturation.

The pH was controlled by the continuous addition of 1N $H_2SO_4$ (theoretical amount, 174.6 ml) using an automatic pH monitoring device, and, at the same rate, feed solution (V) was added.

Feed Solution (V)
13.4 g DL-malic acid
2.7 g $(NH_4)_2SO_4$
2.7 g $K_2HPO_4$
13.4 ml Salt Solution C (II)

Add water and NaOH to make 100 mL of a pH 7.0 solution which was sterilized by filtration using a 0.2 μm filter.

After four hours, oxygen was admixed with the admitted air to maintain the level of dissolved oxygen at 60–70 percent. Ninety minutes later, the oxygen addition was stopped since the dissolved oxygen content began to rise. The stationary growth phase was reached after about 6.5 hours as shown by the following table:

TABLE

Preparation of D-Malic Acid

| Time (hrs) | Added $INH_2SO_4$ | DL-malic acid (ml) | Optical Density | Dissolved Oxygen % | Remarks |
|---|---|---|---|---|---|
| 0 | 0 | 0 | 0.168 | 98 | pH 6.83 |
| 1 | 0 | 0 | 0.230 | 95 | pH 6.94 |
| 2 | 2 | 2.5 | 0.399 | 92 | pH 7.00 |
| 3 | 10 | 11.5 | 0.972 | 84 | pH 7.00 |
| 4 | 34 | 32 | 2.108 | 68 | pH 6.98 |
| 4.8 | 77 | 76.5 | 3.910 | | oxygen added |
| 6 | 130 | 99 | 5.400 | | oxygen added |
| 6.5 | 145 | 100 | 5.870 | 81 | |
| 6.75 | 148 | 100 | 5.920 | 90 | |

After the stationary growth phase had been reached, the cells were removed by centrifugation, and the supernatant was concentrated to 100 ml in vacuo. The pH was brought to 2 by addition of concentrated HCl. The acidified solution was continually extracted with diethyl ether for 24 hours. The extract was concentrated at reduced pressure, and the resulting oily residue dried in vacuo (0.05 torr) yielding 4.64 grams of light yellow crystals.

The aqueous phase was concentrated to dryness and the organic portion of the solids was dissolved in hot acetone. The inorganic salts were separated by filtration. The filtrate was concentrated at reduced pressure, yielding an oil which crystallized after drying at high vacuum. An additional 6.81 g of a light yellow solid was obtained, for a total yield of 11.45 g, about 98%. The chemical purity was >95% by HNMR and the optical purity >99.8% by gas chromatography, obtained by using the procedure described below.

The optical purity of said D-malic acid was determined by procedures well known in the art. After formation of the bis-methyl ester under standard conditions, the free hydroxyl was derivatized by S-α-methoxy-α-trifluoromethyl-phenylacetyl chloride (MTPA-Cl) to afford the corresponding MTPA ester. Capillary vapor phase chromatography analysis afforded the diastereomeric ratio and thence the enantiomeric purity of the parent D-malic acid.

Using a process such as described and illustrated by the above example, D-malic acid can be prepared in enantiomeric excess of 90 percent or higher.

The process of the above example can be repeated with similar results using *Acinetobacter calcoaceticus* ATCC 53927.

The Applicant's invention has been described in detail above with particular reference to preferred embodiments. A skilled practitioner familiar with the above detailed description can make many modifications thereof without departing from the scope and spirit of the claims that follow.

I claim:

1. Process for the preparation of D-malic acid or derivative thereof from a mixture of D-malic acid and L-malic acid, or a mixture of a derivative of said enantiomers, said process comprising:
   (a) incubating said mixture with a resolution agent, said agent comprising a living microorganism or product thereof that assimilates such L-malic acid or derivative thereof but does not assimilate said D-malic acid or derivative thereof, and which can utilize L-malic acid or said derivative thereof as a sole carbon source,
   (b) incubating said inoculated mixture until substantially all of said L-malic acid or derivative is assimilated, and
   (c) thereafter recovering D-malic acid or derivative from the reaction broth thereby produced.

2. Process according to claim 1 wherein said mixture is a racemic mixture of D-malic acid and L-malic acid.

3. Process according to claim 1 wherein said agent is a culture of bacteria capable of assimilating L-malic acid or derivative thereof as a sole carbon source in the substantial absence of added supplements.

4. Process according to claim 3 wherein said bacteria culture is selected from Pseudomonas and Acinetobacter bacteria.

5. Process for the preparation of D-malic acid from a racemic mixture of D-malic acid and L-malic acid, said process comprising:
   (i) subjecting said racemate to the action of bacteria capable of assimilating L-malic acid as a sole carbon source in the substantial absence of added supplements, and incapable of assimilating D-malic acid, until substantially all of said L-malic acid is assimilated, and thereafter
   (ii) recovering D-malic acid from the reaction mixture produces in step (i).

6. Process according to claim 5 wherein said D-malic acid is recovered per se.

7. Process for the recovery of D-malic acid with an enantiomeric excess of at least 95 percent from a racemic mixture of D-malic acid and L-malic acid, said process comprising subjecting said racemate to the action of bacteria capable of assimilating L-malic acid as a sole carbon source in the substantial absence of added supplement, and incapable of assimilating D-malic acid, until substantially all of said L-malic acid is assimilated; said process being conducted in the presence of acid added to replace acidity loss due to the assimilation of L-malic acid sufficient to keep the pH of the reacting mixture from rising above about 9.0.

8. Process according to claim 7 being conducted such that the concentration of D-malic acid in the reacting medium comprising said bacteria is maintained below about 2.5 weight percent based on the weight of the cell free medium.

9. Process according to claim 7 wherein D-malic acid in enantiomeric excess of 95 percent is separated from the reaction broth produced after substantially all of said L-malic acid is assimilated by said bacteria.

* * * * *